United States Patent [19]
Casscells et al.

[11] Patent Number: 6,007,533
[45] Date of Patent: Dec. 28, 1999

[54] ELECTROCAUTERIZING TIP FOR ORTHOPEDIC SHAVE DEVICES

[75] Inventors: Christopher D. Casscells, Greenville, Del.; Hugh R. Sharkey, Woodside, Calif.

[73] Assignee: Oratec Interventions, Inc., Menlo Park, Calif.

[21] Appl. No.: 09/034,885

[22] Filed: Mar. 4, 1998

Related U.S. Application Data

[60] Provisional application No. 60/059,383, Sep. 19, 1997.

[51] Int. Cl.$^6$ .................................................. A61B 17/36
[52] U.S. Cl. ................................ 606/45; 606/41; 606/49; 606/180
[58] Field of Search ........................... 606/41, 42, 45–50, 606/170, 180; 604/21, 22

[56] References Cited

U.S. PATENT DOCUMENTS

| | | |
|---|---|---|
| 2,090,923 | 8/1937 | Wappler . |
| 3,178,728 | 4/1965 | Christensen . |
| 3,579,643 | 5/1971 | Morgan . |
| 3,776,230 | 12/1973 | Neefe . |
| 3,856,015 | 12/1974 | Iglesias . |
| 3,867,728 | 2/1975 | Substad et al. . |
| 3,879,767 | 4/1975 | Substad . |
| 3,886,600 | 6/1975 | Kahn et al. . |
| 3,938,198 | 2/1976 | Kahn et al. . |
| 3,945,375 | 3/1976 | Banko . |
| 3,987,499 | 10/1976 | Scharbach et al. . |
| 3,992,725 | 11/1976 | Homsy . |
| 4,043,342 | 8/1977 | Morrison, Jr. . |
| 4,074,718 | 2/1978 | Morrison, Jr. . |
| 4,085,466 | 4/1978 | Goodfellow et al. . |
| 4,129,470 | 12/1978 | Homsy . |
| 4,134,406 | 1/1979 | Iglesias . |
| 4,224,696 | 9/1980 | Murray et al. . |
| 4,224,697 | 9/1980 | Murray et al. . |
| 4,326,529 | 4/1982 | Doss et al. . |
| 4,344,193 | 8/1982 | Kenny . |
| 4,362,160 | 12/1982 | Hiltebrandt . |

(List continued on next page.)

FOREIGN PATENT DOCUMENTS

| | | |
|---|---|---|
| 0 257 116 A1 | 3/1988 | European Pat. Off. . |
| 0 479 482 A1 | 4/1992 | European Pat. Off. . |
| 0 521 595 A2 | 1/1993 | European Pat. Off. . |
| 0 542 412 A1 | 5/1993 | European Pat. Off. . |
| 0 558 297 A2 | 9/1993 | European Pat. Off. . |
| 0 572 131 A1 | 12/1993 | European Pat. Off. . |
| 0 479 482 B1 | 5/1996 | European Pat. Off. . |
| 0 729 730 A1 | 9/1996 | European Pat. Off. . |
| 0 737 487 A2 | 10/1996 | European Pat. Off. . |
| 2 645 008 | 3/1989 | France . |
| 2 645 008 | 10/1990 | France . |

OTHER PUBLICATIONS

Beadling, L., "Bi–Polar electrosurgical devices: Sculpting the future of arthroscopy", *Orthopedics today*, vol. 17, No. 1, Jan. 1994, 4 pages.

(List continued on next page.)

*Primary Examiner*—Michael Peffley
*Attorney, Agent, or Firm*—Wilson, Sonsoni, Goodrich & Rosati

[57] ABSTRACT

A surgical apparatus includes: a surgical instrument including a housing and a cannula; and a surgical tool including a shaft, and a tip, and a longitudinal member. The longitudinal member is contained within the shaft and is extendable from an interior position to an exterior position in which it is energized in the exterior position to produce a cauterizing action at the tip.

25 Claims, 11 Drawing Sheets

U.S. PATENT DOCUMENTS

| | | |
|---|---|---|
| 4,375,220 | 3/1983 | Matvias . |
| 4,381,007 | 4/1983 | Doss . |
| 4,397,314 | 8/1983 | Vaguine . |
| 4,476,862 | 10/1984 | Pao . |
| 4,483,338 | 11/1984 | Bloom et al. . |
| 4,517,965 | 5/1985 | Ellison . |
| 4,517,975 | 5/1985 | Garito et al. . |
| 4,590,934 | 5/1986 | Malis et al. . |
| 4,593,691 | 6/1986 | Lindstrom et al. . |
| 4,597,379 | 7/1986 | Kihn et al. . |
| 4,601,705 | 7/1986 | McCoy . |
| 4,651,734 | 3/1987 | Doss et al. . |
| 4,811,733 | 3/1989 | Borsanyi et al. . |
| 4,815,462 | 3/1989 | Clark . |
| 4,838,859 | 6/1989 | Strassmann . |
| 4,873,976 | 10/1989 | Schreiber . |
| 4,894,063 | 1/1990 | Nashef . |
| 4,895,148 | 1/1990 | Bays et al. . |
| 4,907,585 | 3/1990 | Schachar . |
| 4,907,589 | 3/1990 | Cosman . |
| 4,924,865 | 5/1990 | Bays et al. . |
| 4,944,727 | 7/1990 | McCoy . |
| 4,950,234 | 8/1990 | Fujioka et al. . |
| 4,955,882 | 9/1990 | Hakky . |
| 4,966,597 | 10/1990 | Cosman . |
| 4,976,709 | 12/1990 | Sand . |
| 4,976,715 | 12/1990 | Bays et al. . |
| 4,998,933 | 3/1991 | Eggers et al. . |
| 5,007,908 | 4/1991 | Rydell . |
| 5,009,656 | 4/1991 | Reimels . |
| 5,085,657 | 2/1992 | Ben-Simhon . |
| 5,085,659 | 2/1992 | Rydell . |
| 5,098,430 | 3/1992 | Fleenor . |
| 5,100,402 | 3/1992 | Fan . |
| 5,103,804 | 4/1992 | Abele et al. . |
| 5,178,620 | 1/1993 | Eggers et al. . |
| 5,186,181 | 2/1993 | Franconi et al. . |
| 5,191,883 | 3/1993 | Lennox et al. . |
| 5,192,267 | 3/1993 | Shapira et al. . |
| 5,201,729 | 4/1993 | Hertzmann et al. . |
| 5,201,730 | 4/1993 | Easley et al. . |
| 5,201,731 | 4/1993 | Hakky ......................................... 606/15 |
| 5,213,097 | 5/1993 | Zeindler . |
| 5,230,334 | 7/1993 | Klopotek . |
| 5,242,439 | 9/1993 | Larsen et al. . |
| 5,242,441 | 9/1993 | Avitall . |
| 5,261,906 | 11/1993 | Pennino et al. . |
| 5,267,994 | 12/1993 | Gentelia et al. . |
| 5,275,151 | 1/1994 | Shockey et al. . |
| 5,284,479 | 2/1994 | de Jong . |
| 5,304,169 | 4/1994 | Sand . |
| 5,308,311 | 5/1994 | Eggers et al. . |
| 5,311,858 | 5/1994 | Adair . |
| 5,320,115 | 6/1994 | Kenna . |
| 5,323,778 | 6/1994 | Kandarpa et al. . |
| 5,334,193 | 8/1994 | Nardella . |
| 5,342,357 | 8/1994 | Nardella . |
| 5,348,554 | 9/1994 | Imran et al. . |
| 5,352,868 | 10/1994 | Denen et al. . |
| 5,354,331 | 10/1994 | Schachar . |
| 5,364,395 | 11/1994 | West, Jr. . |
| 5,366,443 | 11/1994 | Eggers et al. . |
| 5,366,490 | 11/1994 | Edwards et al. . |
| 5,382,247 | 1/1995 | Cimino et al. . |
| 5,397,304 | 3/1995 | Truckai . |
| 5,401,272 | 3/1995 | Perkins . |
| 5,413,575 | 5/1995 | Haenggi . |
| 5,415,633 | 5/1995 | Lazarus et al. . |
| 5,423,806 | 6/1995 | Dale et al. . |
| 5,433,739 | 7/1995 | Sluijter et al. . |
| 5,437,661 | 8/1995 | Rieser . |
| 5,437,662 | 8/1995 | Nardella . |
| 5,451,223 | 9/1995 | Ben-Simhon . |
| 5,458,596 | 10/1995 | Lax et al. . |
| 5,464,023 | 11/1995 | Viera . |
| 5,465,737 | 11/1995 | Schachar . |
| 5,484,403 | 1/1996 | Yoakum et al. . |
| 5,484,432 | 1/1996 | Sand . |
| 5,484,435 | 1/1996 | Fleenor et al. . |
| 5,487,757 | 1/1996 | Truckai et al. . |
| 5,498,258 | 3/1996 | Hakky et al. ............................. 606/15 |
| 5,500,012 | 3/1996 | Brucker et al. . |
| 5,507,812 | 4/1996 | Moore . |
| 5,514,130 | 5/1996 | Baker . |
| 5,524,338 | 6/1996 | Martyniuk et al. . |
| 5,527,331 | 6/1996 | Kresch et al. ......................... 606/170 |
| 5,542,920 | 8/1996 | Cherif Cheikh . |
| 5,569,242 | 10/1996 | Lax et al. . |
| 5,599,346 | 2/1997 | Edwards et al. . |
| 5,630,839 | 5/1997 | Corbett, III et al. . |
| 5,681,282 | 10/1997 | Eggers et al. . |
| 5,683,366 | 11/1997 | Eggers et al. . |
| 5,688,270 | 11/1997 | Yates et al. . |
| 5,697,909 | 12/1997 | Eggers et al. . |
| 5,718,702 | 2/1998 | Edwards ................................... 606/41 |
| 5,782,795 | 7/1998 | Bays ......................................... 604/22 |
| 5,810,809 | 9/1998 | Rydell ..................................... 606/49 |

FOREIGN PATENT DOCUMENTS

| | | |
|---|---|---|
| 3632197 A1 | 3/1988 | Germany . |
| 39 18316 | 3/1990 | Germany . |
| 5-42166 | 2/1993 | Japan . |
| 1 340 451 | 12/1973 | United Kingdom . |
| 2 164 473 | 3/1986 | United Kingdom . |
| WO 82/02488 | 8/1982 | WIPO . |
| WO 85/02762 | 7/1985 | WIPO . |
| WO 92/10142 | 6/1992 | WIPO . |
| WO 93/01774 | 2/1993 | WIPO . |
| WO 93/16648 | 9/1993 | WIPO . |
| WO 93/20984 | 10/1993 | WIPO . |
| WO 95/01814 | 1/1995 | WIPO . |
| WO 95/10981 | 4/1995 | WIPO . |
| WO 95/13113 | 5/1995 | WIPO . |
| WO 95/18575 | 7/1995 | WIPO . |
| WO 95/20360 | 8/1995 | WIPO . |
| WO 95/25471 | 9/1995 | WIPO . |
| WO 95/30373 | 11/1995 | WIPO . |
| WO 95/30377 | 11/1995 | WIPO . |
| WO 95/34259 | 12/1995 | WIPO . |
| WO 96/11638 | 4/1996 | WIPO . |
| WO 96/32051 | 10/1996 | WIPO . |
| WO 96/34568 | 11/1996 | WIPO . |
| WO 96/34571 | 11/1996 | WIPO . |
| WO 96/39914 | 12/1996 | WIPO . |
| WO 97/06855 | 2/1997 | WIPO . |
| WO 98/07468 | 2/1998 | WIPO . |

OTHER PUBLICATIONS

Ellman International Mfg., Inc., 1989, Catalog, pp. 1–15, 20.

Cosset, J.M., Resistive Radiofrequency (Low Frequency) Interstitial Heating (RF Technique), Interstitial Hyperthermia, Dec. 6, 1993, pp. 3–5, 37.

Christian, C. et al., "Allograft Anterior Cruciate Ligament Reconstruction with Patellar Tendon: An Endoscopic Technique", *Operative Techniques in Sports Medicine,* vol. 1, No. 1, Jan. 1993, pp. 50–57.

Houpt, J. et al., "Experimental Study of Temperature Distributions and Thermal Transport During Radiofrequency Current Therapy of the Intervertebral Disc", *Spine,* vol. 21, No. 15, (1996), pp. 1808–1813.

Troussier, B. et al., "Percutaneous Intradiscal Radio–Frequency Thermocoagulation: A Cadaveric Study", *Spine,* vol. 20, No. 15, (Aug. 1995), pp. 1713–1718.

Auhll, Richard A., "The Use of the Resectoscope in Gynecology." Biomedical Business International, Oct. 11, 1990, pp. 91–93.

Gerber et al., Der Orthopade: Offene Laserchirurgie am Bewegungsapparat, vol. 25, (1996) pp. 56–63.

Leu et al., Der Orthopade: Endoskopie der Wirbelsaule: Minimal–invasive Therapie, vol. 21, (1992) pp. 267–272.

Vorwerck et al., Laserablation des Nucleus Pulposus: Optische Eigenschaften von Degeneriertem Bandscheibengewebe im Wellenlangenbereich von 200 bis 2200nm, vol. 151 No. 6, (1989) pp. 725–728.

Kolarik et al., Photonucleolysis of Intervertebral Disc and it's Herniation, vol. 51, (1990) pp. 69–71.

Kolarik et al., Photonucleolysis of Intervertebral Disc and it's Herniation, (1990).

Trimedyne, The Less Invasive Laser Advantage, Omni Spinal Introduction System.

PRNewswire (Dec. 12, 1994), Two Physicians Perform First Outpatient Cervical Disc Procedure Using Laser Technology.

Introduction to the LDD Disc Kit, Oct. 16, 1996.

Mayer et al., Lasers in Percutaneous Disc Surgery: Beneficial Technology or Gimmich?, vol. 25 No. 251 (1993) pp. 38–44.

Schatz et al., Preliminary Experience With Percutaneous Laser Disc Decompression in the Treatment of Sciatica, vol. 38 No. 5, Oct. 1995, pp. 432–436.

Savitz M. A., Same–day Microsurgical Arthroscopic lateral–approach Laser–assisted (SMALL) Fluoroscopic Discectomy, vol. 80, Jun. 1994 pp. 1039–1045.

Bosacco et al., Functional Results of Percutaneous Laser Discectomy, Dec. 1996, pp. 825–828.

Sluijter M.E., The Use of Radiofrequency lesions For Pain Relief in Failed Back Patients, vol. 10 No. 1 (1988).

Cosman et al., Theoretical Aspects of Radiofrequency lesions in the Dorsal Root Entry Zone, vol. 15 No. 6 (1984) pp. 945–950.

Wilkins et al., Neurosurgery: Method of Making Nervous System Lesions, ch. 337, pp. 2490–2499.

Yonezawa et al., The System and Procedure of percutaneous Intradiscal Laser Nucleotomy, vol. 15, No. 5 (1990) pp. 1175–1185.

Kolarik et al., Photonucleolysis of Intervertebral Disc and it's Herniation, (1990).

Gottlob et al.,Lasers in Surgery and Medicine: Holmium: YAG Laser Ablation of Human Intervertebral Disc: Preliminary Evaluation, vol. 12, (1991) pp. 86–91.

Buchelt et al., Lasers in Surgery and Medicine: Fluorescence Guided Excimer Laser Ablation of Intervertebral Discs In Vitro, vol. 11, (1991) pp. 280–286.

Choy et al., Percutaneous Laser Disc Decompression: A New Therapeutic Modality, vol. 17 No. 8, (1992) pp. 949–956.

Sluijter et al., Persistant Pain, Modern Methods of Treatment: Treatment of Chronic Back and neck Pain, vol. 3, (1981) pp. 141–179.

Sluijter, Int Disabil Studies: The use of Radio Frequency Lesions For Pain Relief in Failed Back, vol. 10, Sep. 4, 1996, pp. 37–43.

Shatz et al., CJS JCC Preliminary Experience With Percutaneous Laser Disc Decompression in the Treatment of Sciatica, vol. 38 No. 5, Oct. 1995 pp. 432–436.

Gerber et al., Der Orthopade: Offene Laserchirurgie am Bewegungsapparat, vol. 25, (1996) pp. 56–63.

Gehring W.J., Exploring the Homeobox, (1993), pp. 215–221.

Kelly L.E., Purification and Properties of a 23kDa $Ca2\pm$binding Protein, (1990) 271, pp. 661–666.

Sluyter, Radiofrequency Lesions in the Treatment of Cervical Pain Syndromes, Radionics, Inc. (1989).

Buchelt et al., Lasers in Surgery and Medicine:Erb:YAG and Hol:YAG Laser Ablation of Meniscus and Intervertebral Discs, vol. 12 No. 4, (1992) pp. 375–381.

Phillips et al., JMRI: MR Imaging of Ho: YAG Laser Diskectomy with Histologic Correlation, vol. 3 No. 3, May/Jun. 1993.

Bromm et al., Human Neurobiology: Nerve Fibre Discharges, Cerebral Potentials and Sensations Induced by CO2 laser Stimulation, vol. 3, (1984) pp. 33–40.

Kolarik et al., Photonucleolysis of Intervertebral Disc and it's Herniation, vol. 51, (1990) pp. 69–71.

Wolgin et al., Excimer Ablation of Human Intervertebral Disc at 308 Nanometers, vol. 9, (1989) pp. 124–131.

Davis, Early experience with Laser Disc Decompression, vol. 79 No. 1, (1992) j. Florida M.A.

Quigley et al., Laser Discectomy: Comparison of Systems, vol. 19 No. 3 (1994) pp. 319–322.

Mehta et al., The Treatment of Chronic back Pain: A Preliminary survey of the Effect of Radiofrequency Denervation of the Posterior Vertebral Joints, vol. 34 (1979) pp. 768–775.

Patil et al., Percutaneous Discectomy Using the Electomagnetc Field Focusing Probe: A Feasability Study.

McCulloch et al., CMA Journal: Percutaneous Radiofrequency Lumbar Rhizolysis (rhizotomy), vol. 116, Jan. 8, 1977.

Yonezawa et al., The System and Procedure of Percutaneous Intradiscal Laser Nucleotomy, vol. 15 No. 11 (1990).

Sminia et al., Effects of 434 MHz Microwave Hyperthermia applied to the rat in the region of the cervical Spinal Cord, vol. 3 No. 5 (1987) pp. 441–452.

Sluijter et al., Treatment of Chronic Back and Neck Pain by Percutaneous Therman Lesions, vol. 3 (1981.

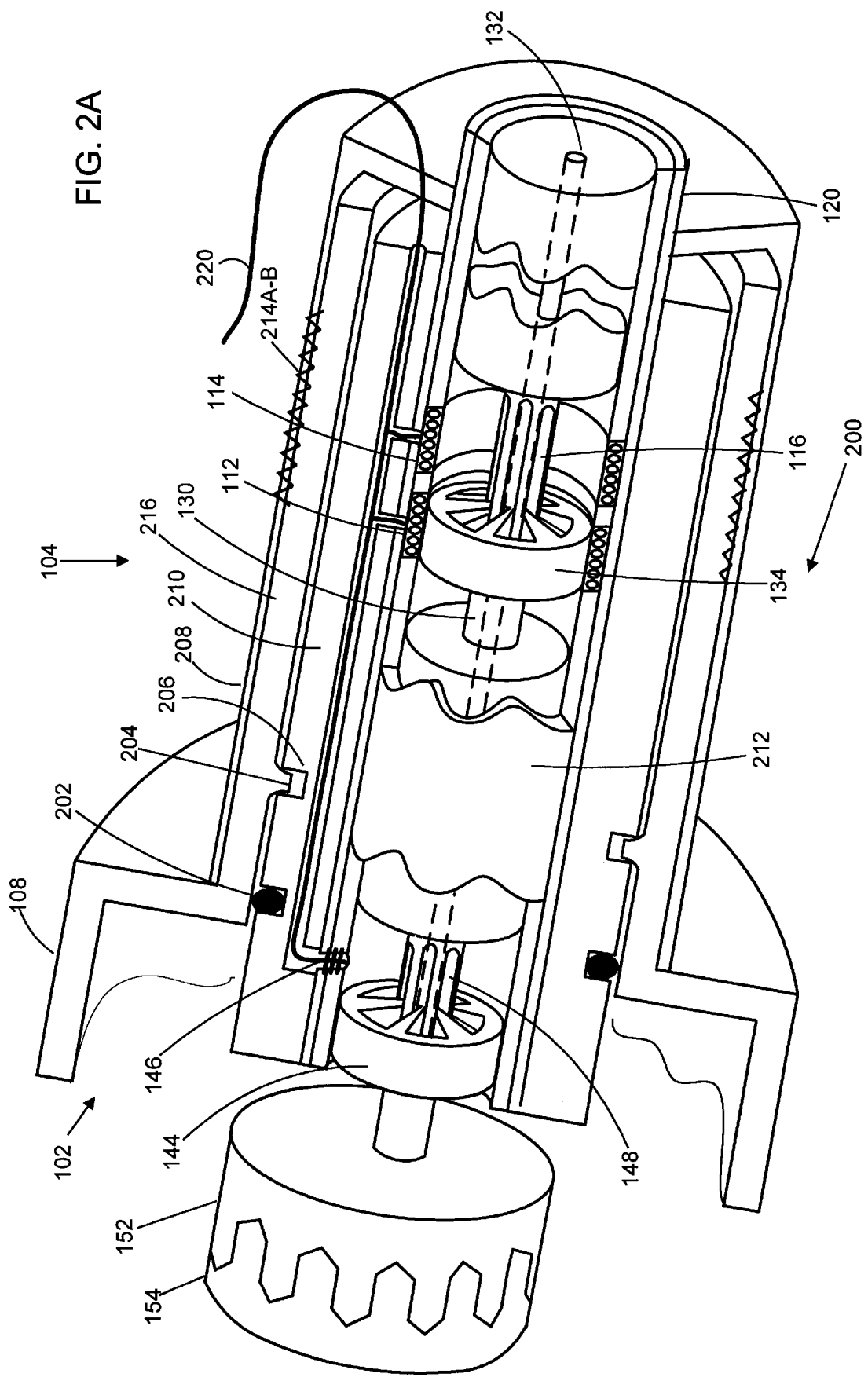

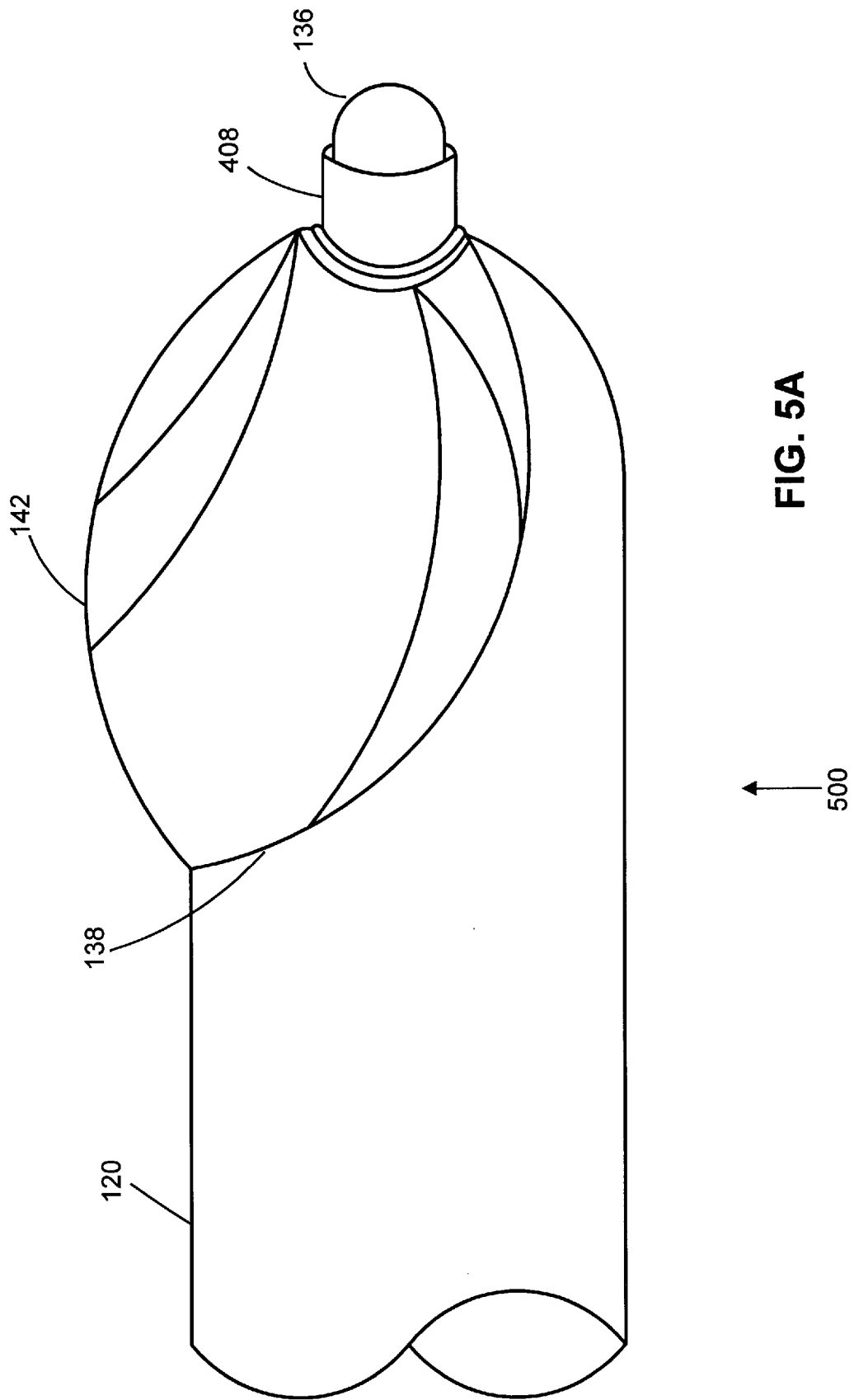

ELECTROCAUTERIZING TIP FOR ORTHOPEDIC SHAVE DEVICES

RELATIONSHIP TO COPENDING APPLICATION

This application is a Utility Application which claims priority to Provisional Application No. 60/059,383, entitled Electrocauterizing Sheath for Arthroscopic Shave Device filed on: Sep. 19 1997. This application is related to Utility Application, Ser. No. 09/066,615, entitled Electrocauterizing Tool for Orthopedic Shave Devices filed on: Apr. 24, 1998; and Utility Application, Ser. No. 09/034,830, entitled Clip on Electrocauterizing Sheath for Orthopedic Shave Devices filed on: Mar. 4, 1998, all of which are incorporated herein by reference.

BACKGROUND OF THE INVENTION

1. Field of the Invention

This invention relates to improved surgical, cutting and cauterizing apparatus and methods for their use.

2. Description of Related Art

Arthroscopic surgery is becoming increasingly popular, because it generally does less damage than open procedures, produces less scarring in and around joints, and results in faster healing and return of the patient to full productivity.

Nevertheless, arthroscopic surgery has its limitations. The surgeon must operate through a narrow tube formed in the body on which surgery is being carried out, which is awkward. Only one probe can be used at a time for many operations. Often the viewing camera is positioned at an angle different from the surgeon's normal gaze. This contrasts with "open surgery" where the surgeon has relative ease of viewing the surgical site and can freely move both hands.

Occasionally, during the performance of an arthroscopic or similar minimally invasive procedure, a surgeon will penetrate a vessel within the surgical site. At this point, the surgeon may desire to cauterize the vessel.

One way of cauterizing the vessel is the use of radio frequency (RF) energy, as described in U.S. Pat. No. 5,100,402 to Fan. Such RF methods offer a quick and relatively easy way of cauterizing penetrated vessels. However, use of current RF cauterizing devices usually requires the surgeon to withdraw the surgical tool being used at the time, and insert a tool for cauterizing the penetrated vessel. This switching of the tools is usually required because of the space limitations involved in arthroscopic surgery.

This switching of tools during surgery can be time consuming, awkward, and potentially dangerous to the patient. Additionally, there is the danger of not being able to locate the penetrated vessel. Therefore, there is the need for an improved surgical apparatus and cutting and cauterizing device and methods for using the apparatus and device to avoid the above-mentioned problems.

SUMMARY OF THE INVENTION

In one aspect, the invention relates to a surgical apparatus, comprising a surgical instrument including a housing and a cannula, and the cannula attached at a proximal end to the housing and defining at a distal end thereof an opening and the housing containing a drive interface; and a surgical tool including a shaft, a tip, and the tip located in the opening, and the shaft contained within the cannula and the shaft defining a longitudinal annulus extending from a proximal end of the shaft to a distal end of the shaft, and the shaft mechanically coupled at the distal end to the tip, and at the proximal end, to the drive interface and the drive interface producing a surgical motion of the tip; and an longitudinal member, including a proximal and a distal end, and the longitudinal member located within the annulus, and the longitudinal member extendable from an interior position in which the distal end is positioned within the tip to an exterior position in which the distal end extends beyond the tip, and energized in the exterior position to produce a cauterizing action at the tip.

In another aspect, the claimed invention relates to a cutting and cauterizing device for connection to a surgical instrument, and the surgical instrument including a drive interface and a first interconnector, and the cutting and cauterizing device comprising a cannula defining at a distal end thereof an opening; a second interconnector, suitable for switchably coupling to a power supply, and the second interconnector located at the proximal end of the cannula and shaped to couple to the first interconnector; and a surgical tool including a shaft and a tip, and the tip located in the opening, and the shaft contained within the cannula, and the shaft defining a longitudinal annulus extending from a proximal end of the shaft to a distal end of the shaft, and the shaft coupled at a distal end to the tip and at a proximal end mechanically coupled to the drive interface to permit a surgical motion of the tip, and a longitudinal member, including a proximal and a distal end, and the longitudinal member located within the annulus, and the longitudinal member extendable from an interior position in which the distal end is positioned within the tip to an exterior position in which the distal end extends beyond the tip, and energized in the exterior position to produce a cauterizing action at the tip.

In yet another aspect, the invention relates to methods of performing surgical procedures, using the surgical apparatus or the cutting and cauterizing device in the course of performing the surgical procedure.

BRIEF DESCRIPTION OF THE DRAWINGS

FIG. 2A is an isometric view of an embodiment of the invention, with a two rotor design, in an unenergized position.

FIG. 5A shows details of a surgical apparatus according to the invention, in the extended position.

DETAILED DESCRIPTION

Figure 1A:
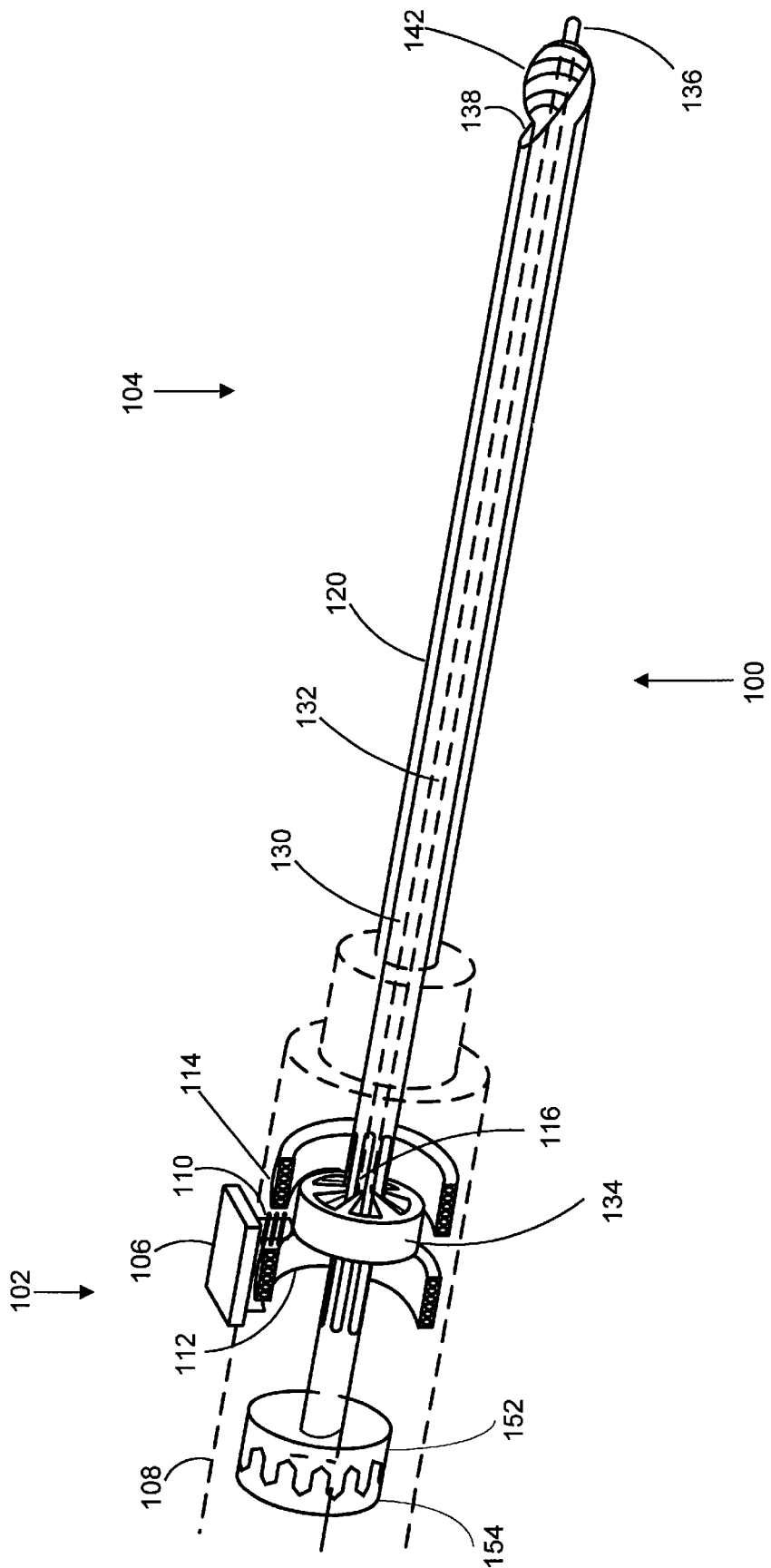
FIG. 1A is an isometric view of an embodiment of the claimed surgical instrument, with a one rotor design.

FIG. 1A shows an isometric view of an embodiment of the inventive surgical apparatus, with a integrated rotor design.

FIG 1A shows surgical apparatus 100, surgical instrument 102, and surgical tool 104. Surgical instrument 102 includes housing 108, cannula 120, brush 110, switch 106, first coil 112, second coil 114, and drive interface 154. Cannula 120 includes opening 138. The surgical tool includes shaft 130, slots 116, longitudinal member 132, first rotor 134, tip 142, distal end 136 of the longitudinal member, and drive coupling 152.

Surgical instrument 102 includes housing 108 and cannula 120 with the cannula attached to the proximal end of the housing. The cannula defines at its distal end an opening 138. The housing includes drive interface 154. Switch 106 is located on housing 108. Surgical tool 104 includes shaft 130 which is contained within the cannula. The shaft has tip 142 attached to the shaft at a distal end of the shaft, and drive coupling 152 attached to the shaft at a proximal end of the shaft. The shaft contains within it longitudinal member 132 and distal end 136 of the longitudinal member. Attached at the proximal end of longitudinal member 132 is first rotor 134. Slots 116 permit the longitudinal motion of the longitudinal member and the attached first rotor with respect to the shaft. Coils 112 and 114 are located adjacent to one another, surrounding the first rotor, within the housing. Also located in the housing is brush 110 which is electrically coupled to distal end 136 of the longitudinal member, via first rotor 134, and longitudinal member 132.

In operation, drive interface 154 engages drive coupling 152 to impart a surgical motion to tip 142 via shaft 130. Switch 106 can alternately energize either first coil 112 or second coil 114 to move longitudinal member 132 along the longitudinal axis of the shaft, thereby extending or retracting the longitudinal member. The movement of longitudinal member 132 is induced through the magnetic coupling between an energized one of coils 112 or 114 and the first rotor 134. When the first coil is energized, the longitudinal member is retracted, causing the distal end 136 of the longitudinal member to retract within the tip. When the second coil is energized, the longitudinal member is extended, causing the distal end of the longitudinal member to extend beyond the tip. When extended, the distal end of the longitudinal member is energized through brush 110, and first rotor 134, thereby producing a cauterizing action.

It should be noted that the surgical motion in any of the embodiments of this invention, can be, for example, rotary, reciprocal, rotary-reciprocal, etc. The shaft, cannula, and longitudinal member can be straight, or can include an arcuate section. In those instances where the surgical tool contains an arcuate section, the shaft and/or longitudinal member may contain a flexible section to accommodate the motion of the shaft and/or longitudinal member.

Figure 1B:
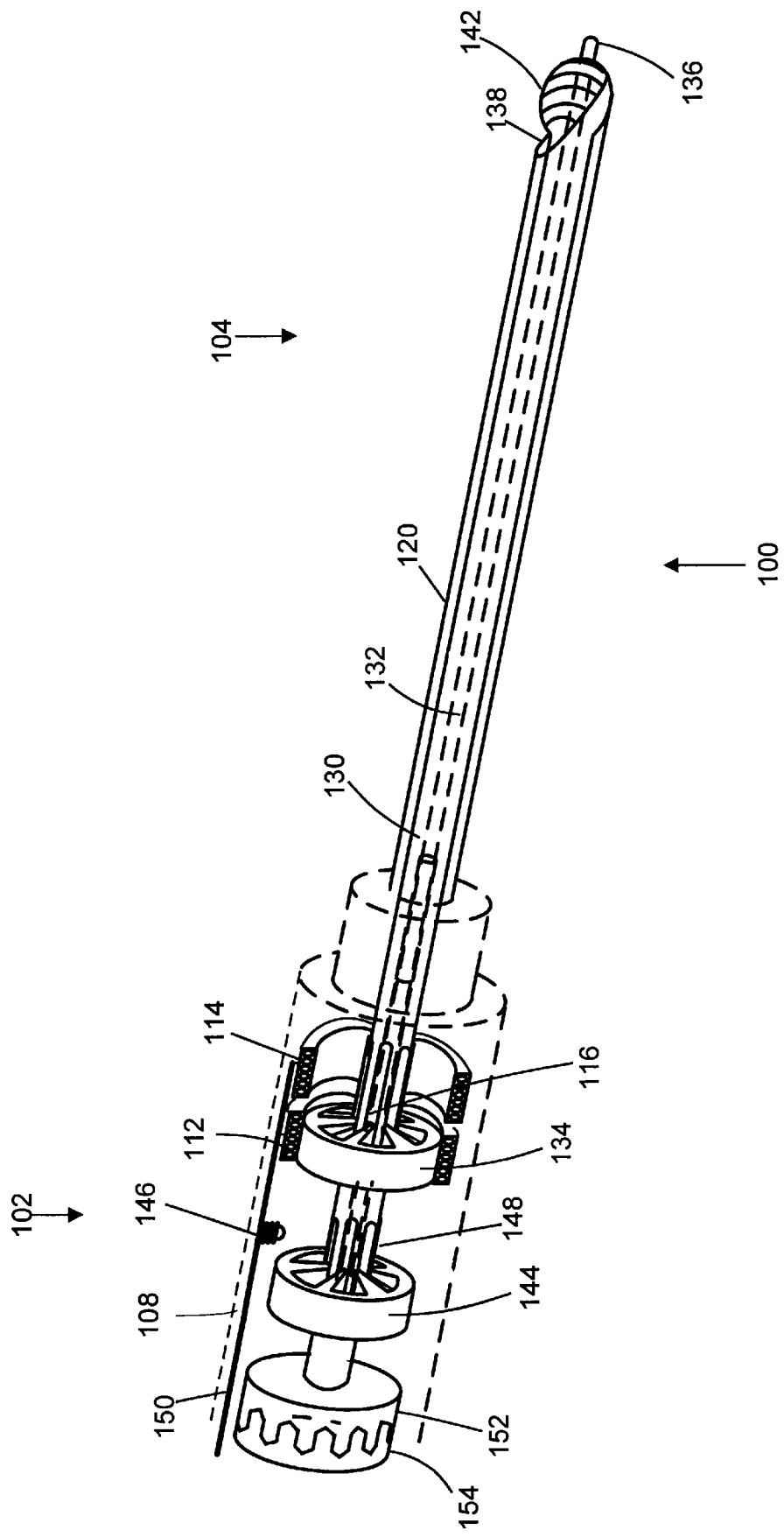
FIG. 1B is an isometric view of another embodiment of the claimed surgical instrument, showing a two rotor design.

FIG. 1B shows an isometric view of another embodiment of the inventive surgical apparatus, with a two rotor design. FIG 1B shows surgical apparatus 100, surgical instrument 102, and surgical tool 104. Surgical instrument 102 includes housing 108, cannula 120, brush 146, first coil 112, second coil 114, electrical conductor 150, and drive interface 154. Cannula 120 includes opening 138. The surgical tool includes shaft 130, slots 116, additional slots 148, longitudinal member 132, first rotor 134, second rotor 144, tip 142, distal end 136 of the longitudinal member, and drive coupling 152.

Surgical instrument 102 includes housing 108 and cannula 120 with the cannula attached to the proximal end of the housing. The cannula defines at its distal end an opening 138. The housing includes drive interface 154. Surgical tool 104 includes shaft 130 which is contained within the cannula. The shaft has tip 142 attached to the shaft at a distal end of the shaft, and drive coupling 152 attached to the shaft at a proximal end of the shaft. The shaft contains within it longitudinal member 132 and distal end 136 of the longitudinal member. Attached at the proximal end of longitudinal member 132 are first rotor 134 and second rotor 144. Slots 116 and additional slots 148 permit the longitudinal motion of the longitudinal member and the attached rotor with respect to the shaft. At the proximal end of the shaft is drive coupling 152. Coils 112 and 114 are located adjacent to one another, surrounding the first rotor, within the housing. Electrical conductor 150 electrically couples brush 146, first electrical coil 112, and second electrical coil 114 to a power supply (not shown). The brush is electrically coupled to distal end 136 of the longitudinal member, via first rotor 134, and longitudinal member 132.

In operation, drive interface 154 engages drive coupling 152 to impart a surgical motion to tip 142 via shaft 130. Either first coil 112 or second coil 114 can be energized to move longitudinal member 132 along the longitudinal axis of the shaft, thereby extending or retracting the longitudinal member. The movement of longitudinal member 132 is induced through the magnetic coupling between either of coils 112 or 114 and the first rotor 134. When extended, the distal end 136 of longitudinal member is energized by a power supply via electrical conductor 150, brush 146, and second rotor 144. This produces a cauterizing action at the distal end of the longitudinal member.

FIG. 2A shows an isometric view of another embodiment of the inventive surgical apparatus, with a two rotor design. The longitudinal member is shown in the retracted position. FIG. 2A shows surgical apparatus 200, surgical instrument 102, and surgical tool 104. Surgical instrument 102 includes housing 108, extended housing portion 216, cannula 120, brush 146, first coil 112, second coil 114, electrical conductor 220, and drive interface 154. The surgical tool includes shaft 130, slots 116, additional slots 148, longitudinal member 132, first rotor 134, second rotor 144, inner alignment piece 212, locking member 210, locking ring 208, and drive coupling 152.

Shaft 130 is contained within cannula 120, and kept separate from the cannula by inner alignment piece 212. The shaft has drive coupling 152 attached to the shaft at a proximal end of the shaft. The shaft contains within it longitudinal member 132. Attached at the proximal end of longitudinal member 132 are first rotor 134 and second rotor 144. Slots 116 and additional slots 148 permit the longitudinal motion of the longitudinal member and the attached rotors with respect to the shaft. Located adjacent to drive coupling 152 is drive interface 154. The cannula, inner alignment piece, shaft, and longitudinal member are held in alignment at their proximal ends to extended housing portion 216 by locking member 210 and locking ring 208. The locking member also has a notch 206, which is located opposite a detent 204 located on an interior surface of the extended housing portion. The locking member additionally includes outer o-ring seal 202, located between the locking member exterior surface and the extended housing portion interior surface. The extended housing portion includes exterior threads 214A, located so as to be opposite interior threads 214B, which are located on locking ring 208.

In operation, cannula 120, inner alignment piece 212, shaft 130, and longitudinal member 132 are held in alignment at their proximal ends to extended housing portion 216 by locking member 210 and locking ring 208. The inner alignment piece serves to locate the shaft within the cannula, and also serves as a bearing for the shaft. Locking member 210 serves to locate the inner alignment piece within extended housing portion 216 through the engagement of notch 206 on the locking member and detent 204 on the interior of the extended housing portion. Locking ring 208 serves to secure the locking member, together with the cannula, inner alignment piece, shaft, and longitudinal member, within the extended housing portion. The locking ring accomplishes this via the cooperative action of its interior threads 214B and exterior threads 214A, which are located on the exterior surface of the extended housing portion. Drive interface 154 engages drive coupling 152 to impart a surgical motion to shaft 130. Outer 0-ring seal 202 serves to prevent transmission of fluids. Either first coil 112 or second coil 114 can be energized to move longitudinal member 132 along the longitudinal axis of the shaft, thereby extending or retracting the longitudinal member. The longitudinal member is shown in the retracted position, with the first rotor 134 aligned within the first coil 112. The movement of longitudinal member 132 is induced through the magnetic coupling between either of coils 112 or 114 and first rotor 134. When extended, the distal end 136 of the longitudinal member is energized by a power supply via electrical conductor 220, brush 146, and second rotor 144. This produces a cauterizing action at the distal end of the longitudinal member.

Figure 2B:
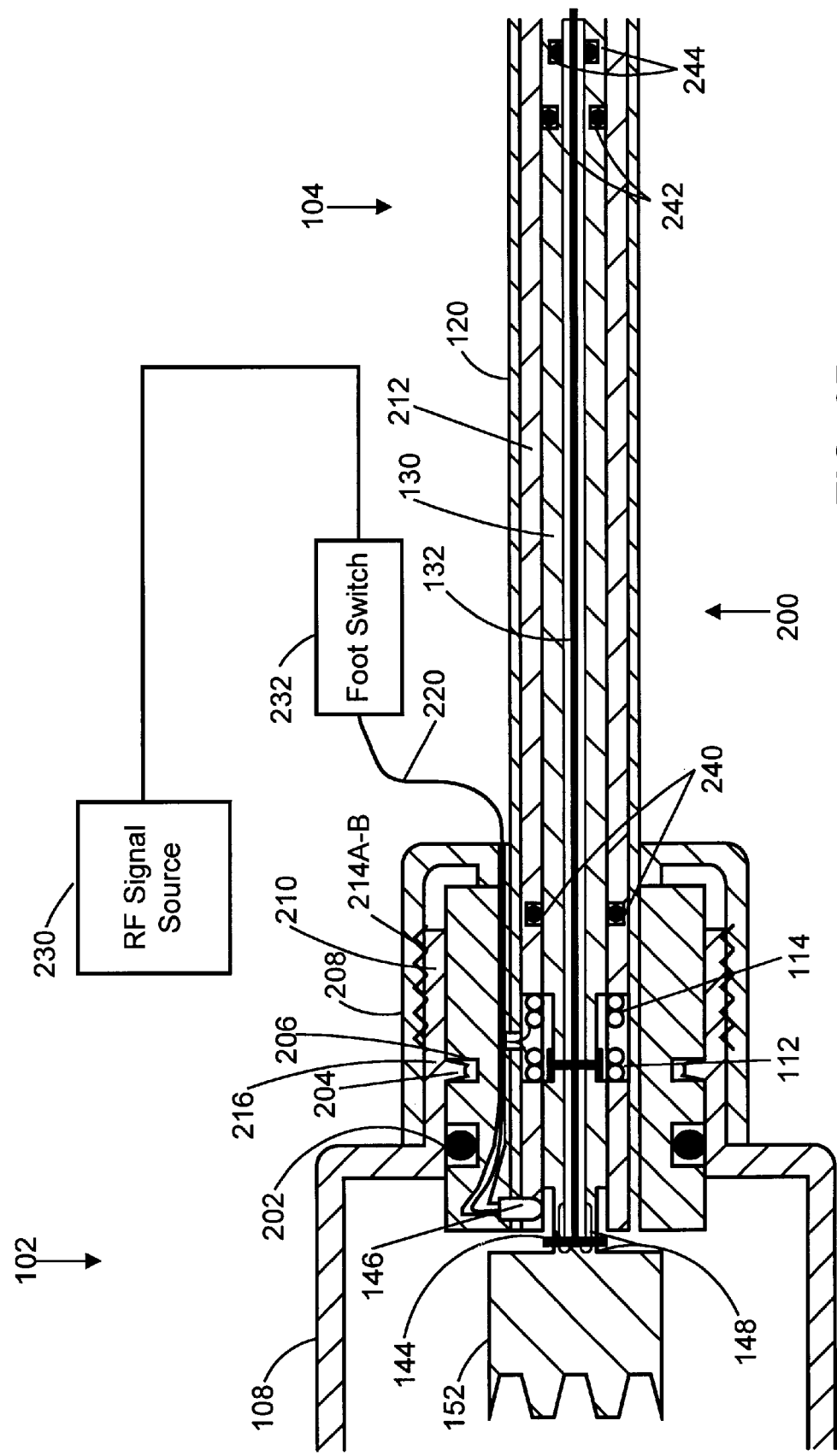
FIG. 2B is a c ross section of the embodiment shown in FIG. 2A.

FIG. 2B shows a cross-section of the embodiment shown in FIG. 2A. The components, structure, and operation of the embodiment shown in FIG. 2B are identical to those shown in FIG. 2A with the following exceptions. Power source 230 supplies power to brush 146 via foot switch 232, and electrical conductor 220. In this cross-section, there is no coupling between brush 146 and second rotor 144, thus leaving longitudinal member 132 unenergized. Also shown are o-ring seals 240, 242, and 244, which serve to prevent transmission of fluids along the shaft or longitudinal member.

Figure 3A:
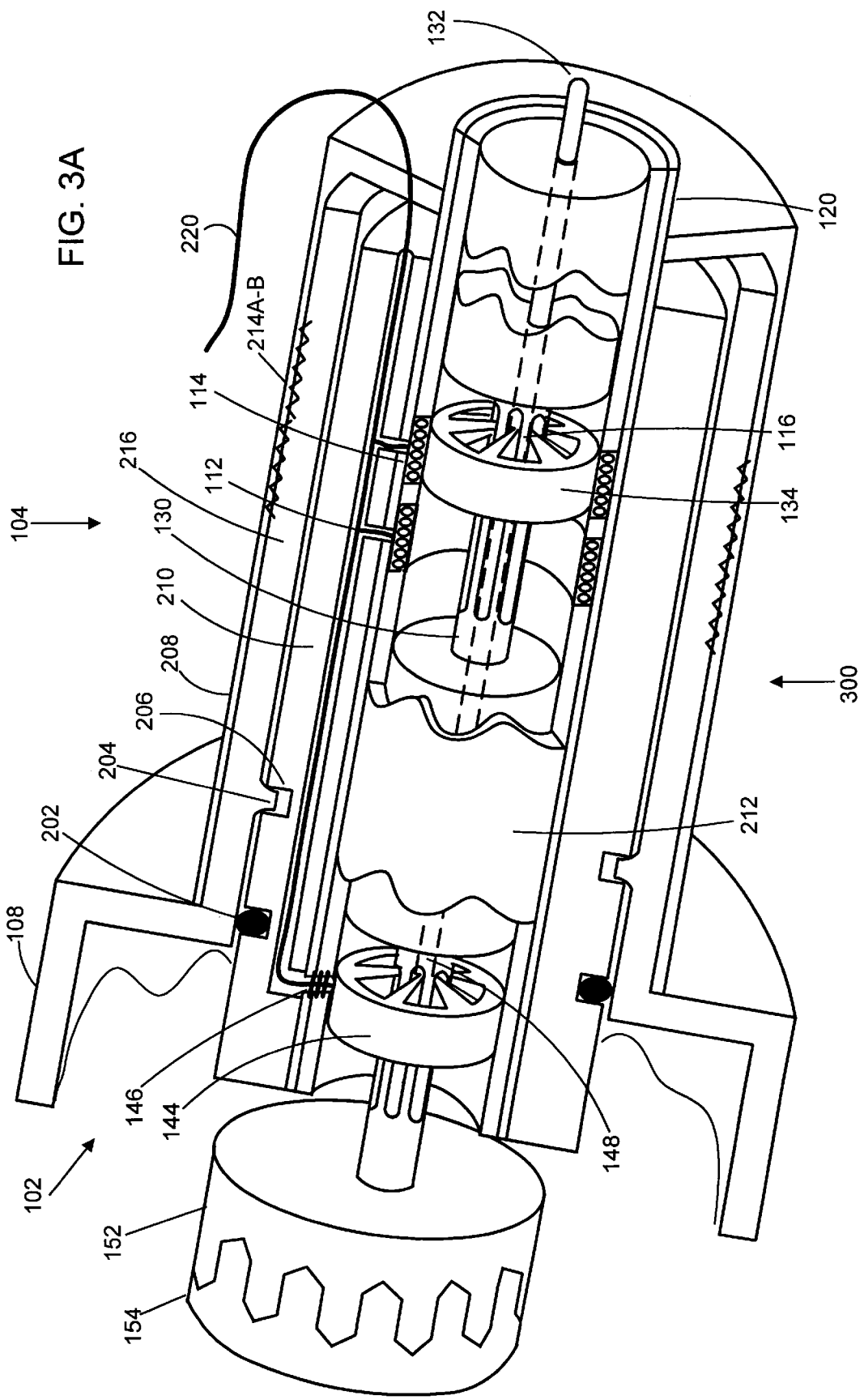
FIG. 3A is an isometric view of the embodiment shown in FIG. 2A, in the energized position.

FIG. 3A. shows a isometric view of the embodiment of surgical apparatus 300 shown in FIG. 2A in the energized position. The components, structure, and operation of the embodiment shown in FIG. 3A are identical to those shown in FIG. 2A with the following exception. FIG. 3A shows the embodiment of FIG. 2A in the energized position, with the longitudinal member extended. The longitudinal member is shown in the extended position, with the first rotor 134 aligned within the second coil 114. The movement of longitudinal member 132 is induced through the magnetic coupling between second 114 and first rotor 134.

Figure 3B:
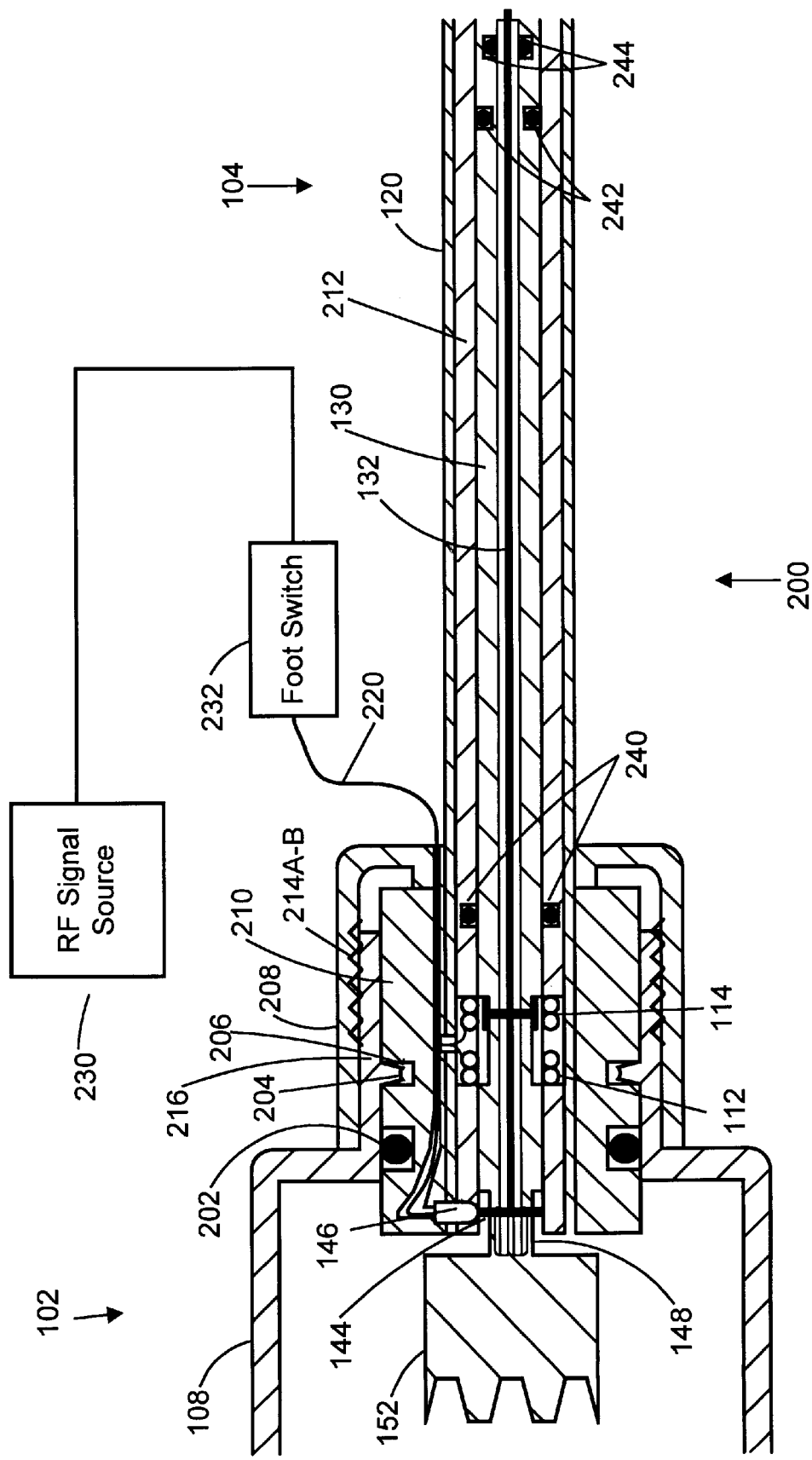
FIG. 3B is a cross-section of the embodiment shown in FIG. 3A.

FIG. 3B. shows a cross-sectional view of the embodiment shown in FIG. 3A. The components, structure, and operation of the embodiment shown in FIG. 3A are identical to those shown in FIG. 2A with the following exceptions. Power source 230 supplies power to brush 146 via foot switch 232, and electrical conductor 220. In this cross-section, the longitudinal member is in the extended position. In the extended position, there is a electrical coupling between brush 146 and second rotor 144, thus energizing the longitudinal member. Also shown are o-ring seals 240, 242, and 242, which serve to prevent transmission of fluids along the shaft or longitudinal member.

Figure 4A:
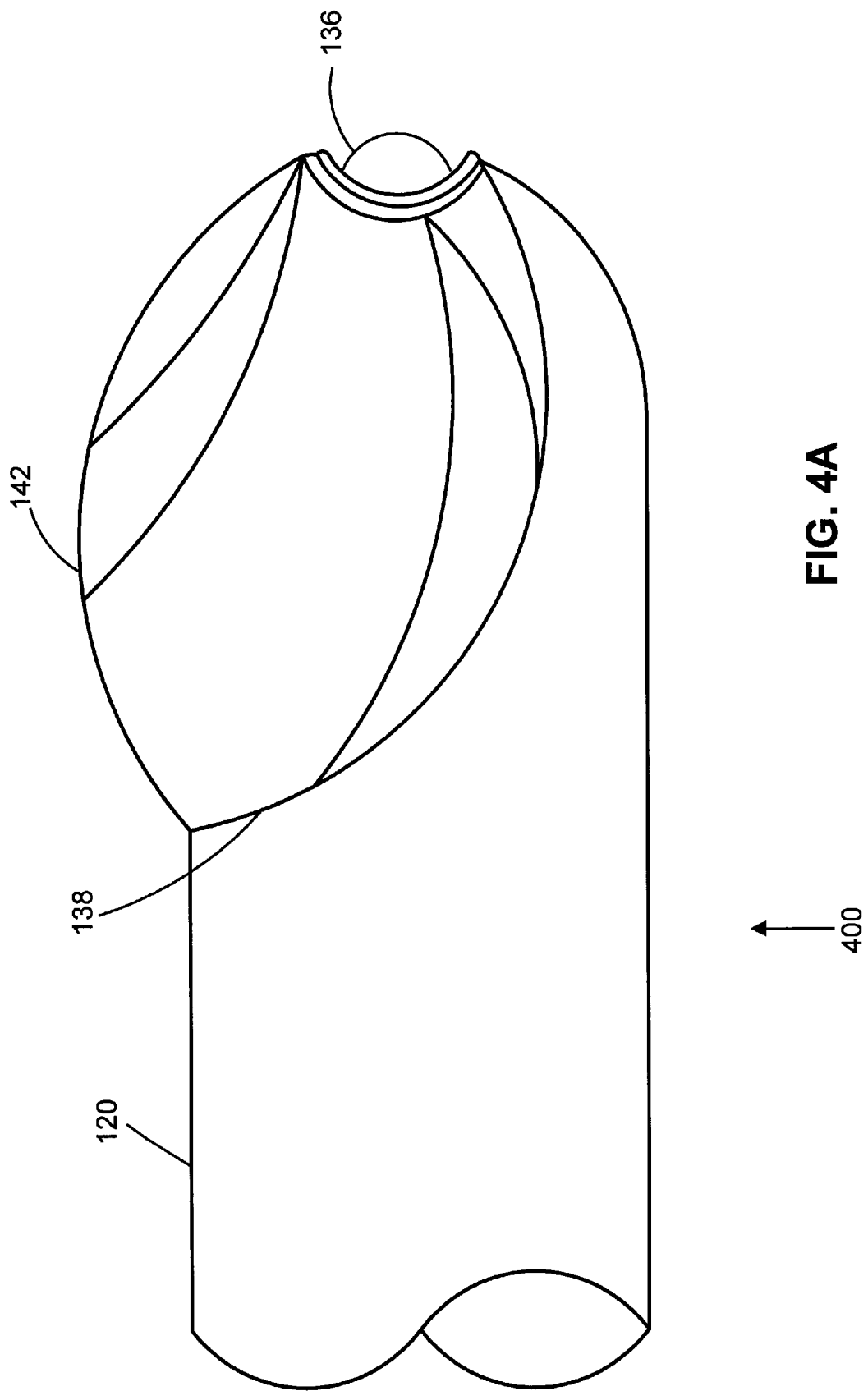
FIG. 4A is an isometric view of the embodiment shown in FIG. 2A, in the retracted position.

FIG. 4A shows surgical apparatus 400, with details of the tip and the longitudinal member in the retracted position. Shown are tip 142, distal end 136 of the longitudinal member, cannula 120, and opening 138.

Cannula 120 defines at its distal end an opening 138. Tip 142 is located within the opening. The tip contains within it distal end 136 of the longitudinal member.

In operation, a surgical motion may be imparted to tip 142. Distal end 136 of the longitudinal member is shown in the retracted, unenergized position.

Figure 4B:
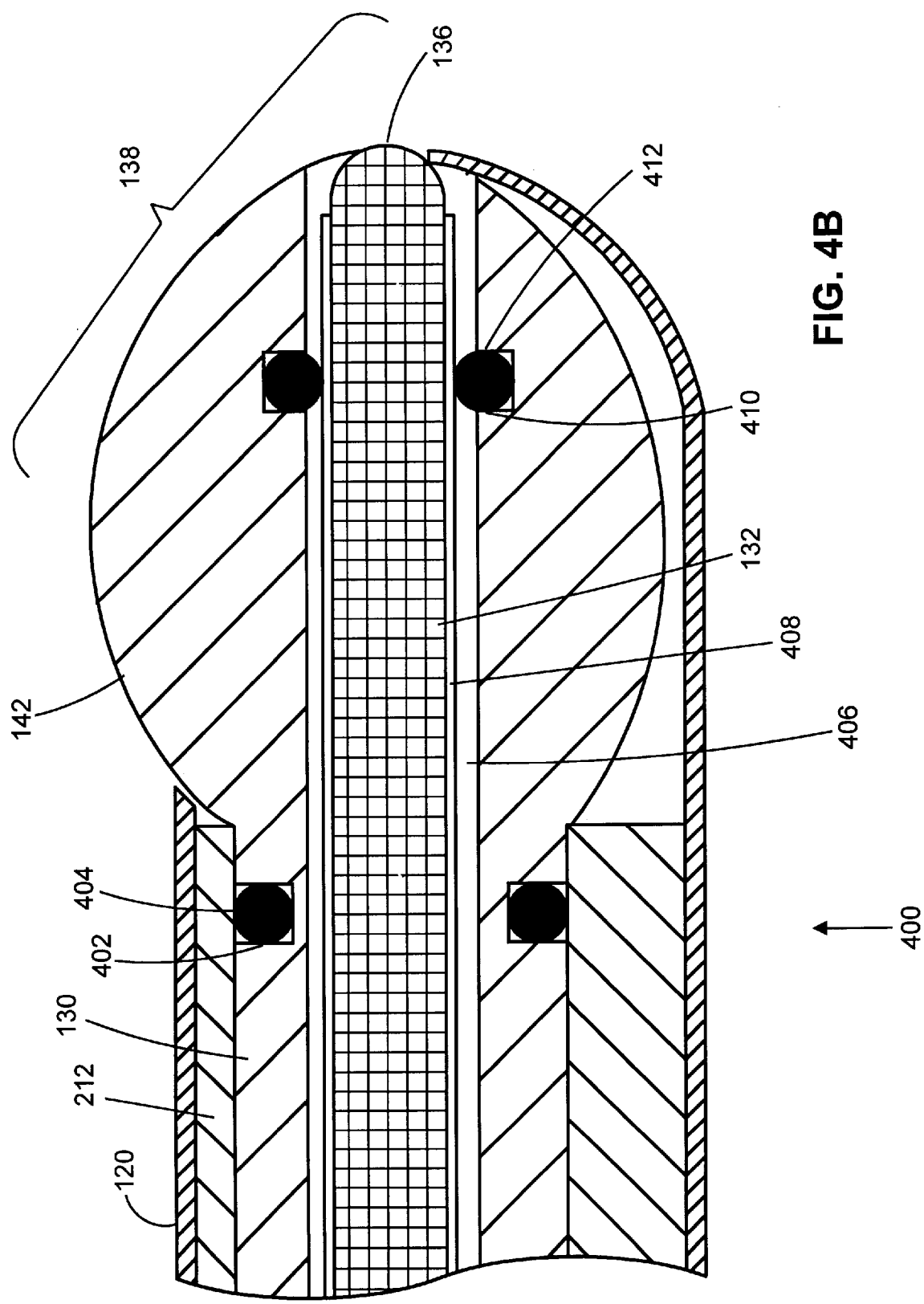
FIG. 4B is a cross-section of the embodiment shown in FIG. 4A.

FIG. 4B shows a cross-sectional view of surgical apparatus 400 shown in FIG. 4A, with details of the tip and the longitudinal member in the retracted position. Shown are shaft 130, inner alignment piece 212, tip 142, longitudinal member 132, distal end 136 of the longitudinal member, cannula 120, longitudinal annulus 406, insulating layer 408, and opening 138. Also shown are distal o-ring seal 404, and tip o-ring seal 412.

Cannula 120 defines at its distal end an opening 138. Tip 142 is located within the opening. Shaft 130 is contained within cannula 120, is kept separate from the cannula by inner alignment piece 212, and is attached to the tip at the distal end of the shaft. The shaft contains within it longitudinal annulus 406. Within the longitudinal annulus is the longitudinal member 132, which is contained within insulating layer 408. The tip contains within it distal end 136 of the longitudinal member. The distal end of the shaft also includes distal O-ring seat 402. Distal O-ring seal 404 is located within the distal o-ring seat, and is in contact with the interior surface of the inner alignment piece. The tip also includes tip O-ring seat 410. Tip O-ring seal 412 is located within the tip o-ring seat, and is in contact with the exterior surface of the insulating layer.

In operation, a surgical motion may be imparted to tip 142 by shaft 130. Distal end 136 of longitudinal member 132 is shown in the retracted, unenergized position. Together shaft 130, inner alignment piece 212, distal O-ring seat 402, distal O-ring seal 404, tip O-ring seat 410, and tip O-ring seal 412 serve to produce a seal that prevents transmission of fluids.

FIG. 5A shows surgical apparatus 500, with details of the tip and the longitudinal member in the extended position. Shown are tip 142, distal end 136 of the longitudinal member, insulating layer 408, cannula 120, and opening 138.

Cannula 120 defines at its distal end an opening 138. Tip 142 is located within the opening. The tip contains within it distal end 136 of the longitudinal member, which is partially surrounded by insulating layer 408.

In operation, a surgical motion may be imparted to tip 142. In the energized position, distal end 136 of the longitudinal member is extended, thus permitting a cauterizing action at the distal end of the longitudinal member.

Figure 5B:
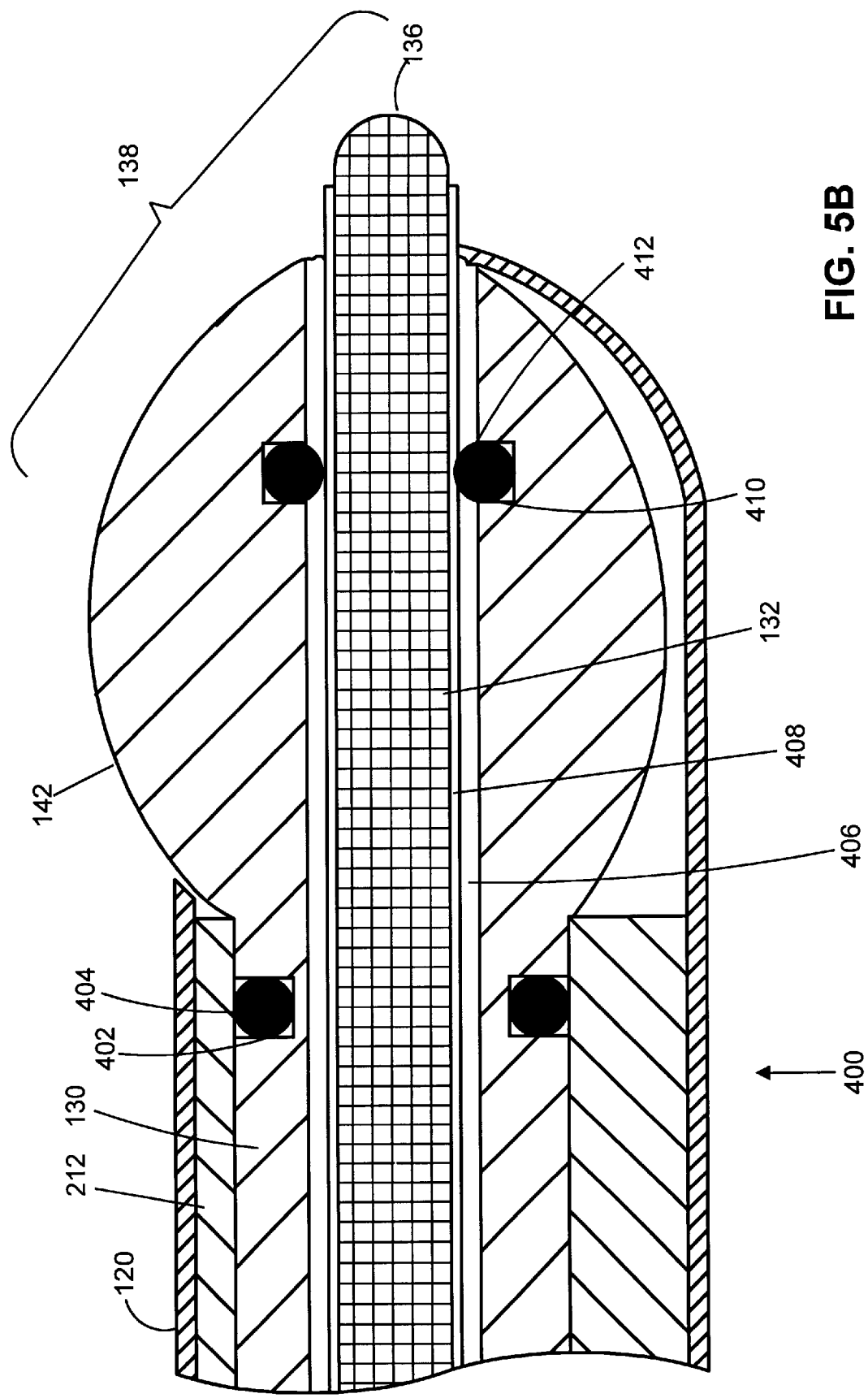
FIG. 5B is a cross-section of the embodiment shown in FIG. 5A.

FIG. 5B shows a cross-sectional view of the surgical apparatus shown in FIG. 5A, with details of the tip and the longitudinal member in the extended position. The components, structure, and operation of the embodiment shown in FIG. 5B are identical to those shown in FIG. 4B with the following exception. FIG. 5B shows the embodiment of FIG. 4B in the energized position, with the longitudinal member extended.

Figure 6:
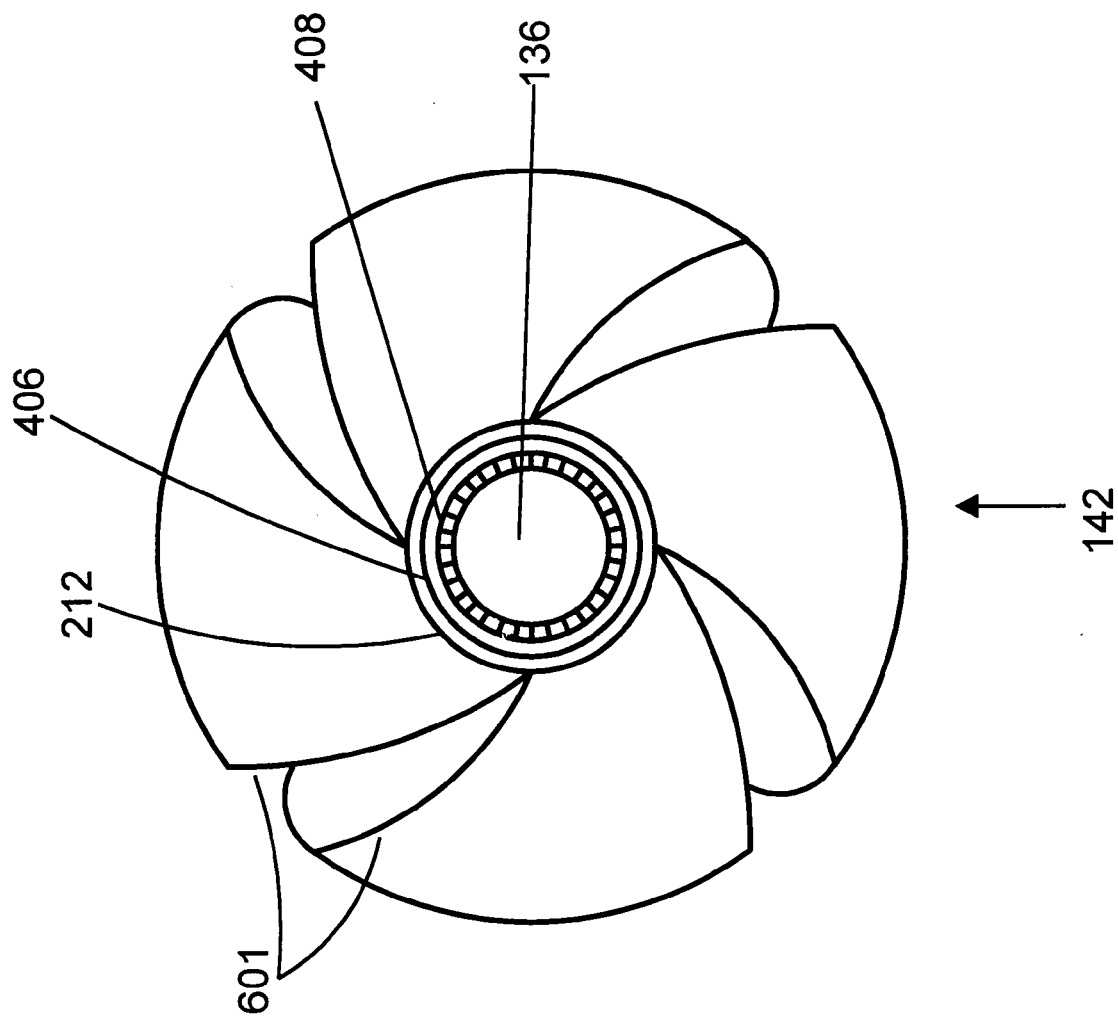
FIG. 6 is an end on view of a portion of the surgical apparatus according to the invention.

FIG. 6 shows an end-on view of one embodiment of tip 142 according to the invention. Shown are distal end 136 of the longitudinal member, insulating layer 408, longitudinal annulus 406, inner alignment piece 212, and cutting edges 601.

Tip 142 contains within it alignment piece 212, longitudinal annulus 406, and distal end 136 of the longitudinal member, which is partially surrounded by insulating layer 408. Cutting edges 601 are present on tip 142.

In operation, a surgical motion may be imparted to tip 142, with cutting edges 601 performing cutting action. In the energized position, distal end 136 of the longitudinal member is extended, thus permitting a cauterizing action at the distal end of the longitudinal member.

It will be apparent to those skilled in the art that various modifications and variations can be made in the apparatus and methods of the present invention without departing from the spirit or scope of the invention. Thus, it is intended that the present invention cover the modifications and variations of this invention provided they come within the scope of the appended claims and their equivalents.

What is claimed is:

1. A surgical apparatus, comprising:
   a surgical instrument including a housing and a cannula, and the cannula attached at a proximal end to the housing and defining at a distal end thereof an opening and the housing containing a drive interface; and
   a surgical tool including a shaft, a tip, and the tip located in the opening, and the shaft contained within the cannula and the shaft defining a longitudinal annulus extending from a proximal end of the shaft to a distal end of the shaft, and the shaft mechanically coupled at the distal end to the tip, and at the proximal end, to the drive interface and the drive interface producing a surgical motion of the tip; and
   a longitudinal member, including a proximal and a distal end, and the longitudinal member located within the annulus, and the longitudinal member extendable from an interior position in which the distal end is positioned within the tip to an exterior position in which the distal end extends beyond the tip, and is adapted to be energized in the exterior position to produce a cauterizing action at the tip.

2. The surgical apparatus of claim 1, wherein the longitudinal member includes a generally insulating portion along its length, and its distal end is generally conducting.

3. The surgical apparatus of claim 2, wherein the longitudinal member's generally insulating portion forms a bearing surface between an exterior surface of the longitudinal member and an interior surface of the longitudinal annulus of the shaft.

4. The surgical apparatus of claim 1 wherein the surgical instrument further comprises:
   a brush coupled to the housing; and
   a commutator coupled to the longitudinal member, and the brush electrically connectable to the commutator to energize the longitudinal member.

5. The surgical apparatus of claim 1, further comprising:
   a first magnetic member stationary with respect to the housing; and
   a second magnetic member coupled to the longitudinal member, and one of the first and second magnetic members switchably energizable, to produce a magnetic field, and another of the first and second magnetic members responsive to the magnetic field to move the longitudinal member between the interior and the exterior positions.

6. The surgical apparatus of claim 5, wherein the first magnetic member includes a first and second coil, and the first coil is switchably energizable to produce a first magnetic field, and the second coil is switchably energizable to produce a second magnetic field, and the second magnetic member includes a permanent magnet responsive to the first magnetic field to move the longitudinal member to the interior position, and the permanent magnet responsive to the second magnetic field to move the longitudinal member to the exterior position.

7. The surgical apparatus of claim 1, further comprising:
   an interconnector, which serves to removably connect the surgical tool to the housing.

8. The surgical apparatus of claim 7, wherein the interconnector further comprises:
   a first magnetic member stationary with respect to the interconnector; and
   a second magnetic member coupled to the longitudinal member, and one of the first and second magnetic members is switchably energizable, to produce a magnetic field, and another of the first and second magnetic members responsive to the magnetic field to move the longitudinal member between the interior and the exterior positions.

9. The surgical apparatus of claim 1 wherein the shaft is generally conductive.

10. The surgical apparatus of claim 1 wherein the shaft is generally non-conductive.

11. The surgical apparatus of claim 1 wherein the shaft is made from a material selected from the material group consisting of stainless steel and plastic.

12. The surgical apparatus of claim 1, further comprising:
   an inner seal located at the tip, and positioned between the longitudinal member and the tip to prevent the flow of fluids in the longitudinal annulus.

13. The surgical apparatus of claim 1, further comprising:
   an outer seal, located at the distal end of the shaft between the shaft and the cannula to prevent the flow of fluids.

14. A cutting and cauterizing device for connection to a surgical instrument including a drive interface and a first interconnector, the cutting and cauterizing device comprising:
   a cannula defining at a distal end thereof an opening;
   a second interconnector, suitable for switchably coupling to a power supply, and the second interconnector located at the proximal end of the cannula and shaped to couple to the first interconnector; and
   a surgical tool including a shaft and a tip, and the tip located in the opening, and the shaft contained within the cannula, and the shaft defining a longitudinal annulus extending from a proximal end of the shaft to a distal end of the sheet, and the shaft coupled at a distal end to the tip and at a proximal end adapted to be mechanically coupled to the drive interface to permit a surgical motion of the tip,
   a longitudinal member, including a proximal and a distal end, and the longitudinal member located within the annulus, and the longitudinal member extendable from an interior position in which the distal end is positioned within the tip to an exterior position in which the distal end extends beyond the tip, and is adapted to be energized in the exterior position to produce a cauterizing action at the tip.

15. The cutting and cauterizing device of claim 14, wherein the longitudinal member includes a generally insulating portion along its length, and its distal end is generally conducting.

16. The cutting and cauterizing device of claim 15, wherein the generally insulating portion of the longitudinal member forms a bearing surface between an exterior surface of the longitudinal member and an interior surface of the longitudinal annulus of the shaft.

17. The cutting and cauterizing device of claim 14, wherein the first interconnector includes:
   a first magnetic member stationary with respect to the first interconnector; and a second magnetic member coupled to the longitudinal member, and one of the first and second magnetic members is switchably energizable, to produce a magnetic field, and another of the first and second magnetic members is responsive to the magnetic field to move the longitudinal member between the interior and the exterior positions.

18. The cutting and cauterizing device of claim 17, wherein the first magnetic member includes a first and second coil, and the first coil switchably energizable to produce a first magnetic field, and the second coil switchably energizable to produce a second magnetic field, and the second magnetic member includes a permanent magnet responsive to the first magnetic field to move the longitudinal member to the interior position, and the permanent magnet responsive to the second magnetic field to move the longitudinal member to the exterior position.

19. The cutting and cauterizing device of claim 14 wherein the shaft is generally conductive.

20. The cutting and cauterizing device of claim 14 wherein the shaft is generally non-conductive.

21. The cutting and cauterizing device of claim 14 wherein the shaft is made from a material selected from the material group consisting of stainless steel and plastic.

22. The cutting and cauterizing device of claim 14, further comprising:

an inner seal located at the tip, and positioned between the longitudinal member and the tip to prevent the flow of fluids in the longitudinal annulus.

23. The cutting and cauterizing device of claim 14, further comprising:

an outer seal, located at the distal end of the shaft between the shaft and the cannula to prevent the flow of fluids.

24. A method of performing a surgical procedure, comprising using the surgical apparatus of claim 1 in the course of performing the surgical procedure.

25. A method of performing a surgical procedure, comprising using the cutting and cauterizing device of claim 14 in the course of performing the surgical procedure.

* * * * *

UNITED STATES PATENT AND TRADEMARK OFFICE
CERTIFICATE OF CORRECTION

PATENT NO.    : 6,007,533
DATED         : December 28, 1999
INVENTOR(S)   : Christopher D. Casscells and Hugh R. Sharkey It is certified that error appears on the above-identified patent and that said Letters Patent is hereby corrected as shown below:

Column 8, line 44, "sheet" should be --shaft--.

Signed and Sealed this

First Day of August, 2000

*Attest:*

Q. TODD DICKINSON

*Attesting Officer*          *Director of Patents and Trademarks*